United States Patent [19]

Mondet et al.

[11] Patent Number: 5,318,995
[45] Date of Patent: Jun. 7, 1994

US005318995A

[54] COSMETIC COMPOSITION CONTAINING AS A THICKENING AGENT A POLYMER HAVING A SLIGHT PROPORTION OF UNITS HAVING IONIC GROUPS

[75] Inventors: Jean Mondet, Drancy; Christos Papantoniou, Montmorency; Guy Vanlerberghe, Montjay la Tour, all of France

[73] Assignee: L'Oreal, Paris, France

[21] Appl. No.: 535,204

[22] Filed: Jun. 8, 1990

[30] Foreign Application Priority Data

Jun. 9, 1989 [LU] Luxembourg .............................. 87534

[51] Int. Cl.⁵ .......................... A61K 7/42; A61K 7/44; A61K 7/48; A61K 9/10
[52] U.S. Cl. .................................... 514/772.1; 424/59; 424/60; 514/844; 514/847; 514/938; 514/772.4

[58] Field of Search ................................. 514/937, 938

[56] References Cited

U.S. PATENT DOCUMENTS 4,927,627  5/1990  Schrader et al. ................... 514/938

OTHER PUBLICATIONS

Chemical Abstracts, 1983, vol. 99, 218,417g, Salamone.

*Primary Examiner*—Dale R. Ore
*Attorney, Agent, or Firm*—Cushman, Darby & Cushman

[57] ABSTRACT

A cosmetic composition or a support for a cosmetic composition, in the form of a water-in-oil emulsion, contains as a thickening agent, at least one copolymer containing a low or slight amount of units containing ionic groups.

17 Claims, No Drawings

COSMETIC COMPOSITION CONTAINING AS A THICKENING AGENT A POLYMER HAVING A SLIGHT PROPORTION OF UNITS HAVING IONIC GROUPS

The present invention relates to a cosmetic composition or support for cosmetic compositions, in the form of a water-in-oil type emulsion, containing as a thickening agent at least one copolymer containing a slight amount of units containing ionic groups.

It is known that cosmetic compositions, in the form of water-in-oil type emulsions, are provided in the form of milks or creams. Compositions in the form of milks are fluid emulsions. Creams are thick emulsions having a viscosity generally greater than 1.5 Pa.s.

The preparation of creams in the form of water-in-oil type emulsions requires thickening the continuous oily phase of the emulsion. Generally, such thickening is accomplished by incorporating a wax in the oily phase. However, creams thickened with waxes have a feel or touch which is generally considered to be disagreeable.

The present invention relates to the preparation of thick creams of the water-in-oil type which do not exhibit this disadvantage. In the creams of the present invention, thickening is accomplished using copolymers containing a slight amount of ionic or ionizable groups.

The present invention thus relates to a cosmetic composition or a cosmetic composition support in the form of a thick emulsion of the water-in-oil type, characterized by the fact that it contains a thickening agent constituted by at least one copolymer comprising units of the formula

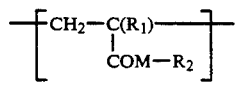  (I)

wherein
M is an oxygen atom or a —N(R$_3$)— group,
R$_1$ represents hydrogen or —CH$_3$,
R$_2$ is a saturated, linear or branched hydrocarbon chain having 4-22 carbon atoms,
R$_3$ represents hydrogen or a saturated, linear or branched hydrocarbon chain having 1-22 carbon atoms, and units of the formula

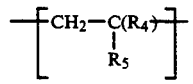  (II)

wherein
(a) R$_4$ represents hydrogen or —CH$_3$, and R$_5$ represents a —CO—X—Z—Y group wherein X represents an oxygen atom or a —N(R$_6$)— group wherein R$_6$ represents hydrogen or a saturated hydrocarbon chain having 1-22 carbon atoms, Z represents a linear or branched saturated hydrocarbon chain having 2-22 carbon atoms, optionally interrupted by —NH-groups or by —O-heteroatoms, and Y represents —COOH or —SO$_3$H, or
(b) R$_4$ represents hydrogen and R$_5$ represents —SO$_3$H, —CH$_2$SO$_3$H or —C$_6$H$_4$—SO$_3$H, it being understood that the said copolymer contains, in units, from 90 to 99 percent of units of formula I, the other units being constituted by units of formula II, that the said —COOH, —SO$_3$H, —CH$_2$SO$_3$H and —C$_6$H$_4$SO$_3$H groups present are under a partially or totally salified form, and it being further understood that when R$_5$ represents —C$_6$H$_4$SO$_3$H, M represents a —N(R$_3$)— group.

Representative preferred copolymers useful as thickening agents in accordance with the present invention, include in particular, those which do not contain any —SO$_3$H groups, free or salified and those which do not contain any -COOH groups, free or salified.

The copolymers employed in accordance with the present invention can also contain at the same time —SO$_3$H groups, free or salified, and —COOH groups, free or salified.

The copolymers employed as thickening agents in accordance with the present invention can be obtained by the copolymerization of monomers of formula III,

  (III)

wherein R$_1$, M and R$_2$ have the meanings given above, with monomers of formula IV

  (IV)

wherein R$_4$ and R$_5$ have the meanings given above.

It is also possible to prepare certain copolymers of the present invention by the copolymerization of styrene and monomers of formula III bis,

  (III bis)

wherein R$_1$, R$_2$ and R$_3$ have the meanings given above, thereby producing a corresponding copolymer which is submitted to the action of a sulfonation agent thereby yielding a copolymer whose units have ionic groups having the formula V

  (V)

The copolymerization reaction is carried out in accordance with conventional procedures, for example, in solution, in suspension or in emulsion.

The molecular mass of the copolymers of the present invention varies generally from 5,000 to about 500,000.

The monomers of formulas III, III bis and IV are known products or can be prepared in accordance with known methods.

In the particular embodiments of the present invention, the copolymers employed as thickening agents can also exhibit the following characteristics, taken singly or in combination:

R$_2$ represents an alkyl group having 4 to 18 carbon atoms;

R$_3$ is hydrogen or an alkyl group having 1-18 carbon atoms; and

Z represents alkylene having 2-22 carbon atoms.

Representative monomers which are the origin of the units of formula I include, for example, the acrylates and methacrylates of hexyl, 2-ethylhexyl, dodecyl and octadecyl as well as the corresponding acrylamides and methacrylamides (with M=NH rather than O). N- ethyl-N-dodecyl (and the N-butyl N-dodecyl) acrylamides and methacrylamides can also be employed.

Representative monomers leading to units of formula II include, for example, 2-acrylamido-2-methyl propane sulfonic acid, (10-acrylamido-10-methyl) decanoate of 2-sulfoethyl, 2-sulfoethyl methacrylate, vinyl sulfonic acid and allyl sulfonic acid.

In the copolymers employed in accordance with the present invention, the units of formula II must be at least in part present in the form of salts, the salification being able to be total. The salts are principally metallic salts such as salts of alkali metals, alkaline earth metals, zinc salts or even amine salts such as salts of triethanolamine, salts of 2-amino-2-methyl-1-propanol, salts of 2-amino-2-methyl-1,3-propanediol and the like. Representative metallic salts include, principally, salts of lithium, potassium, sodium, zinc, calcium, magnesium and the like.

In the cosmetic compositions or cosmetic composition supports, according to the present invention, the amount of thickening copolymers, such as defined above, is generally from 0.05 to 5 weight percent, and preferably from 0.1 to 2 weight percent based on the total weight of the composition or support.

Because the major portion of the units in the thickening copolymers employed in accordance with the present invention are units of formula I, these copolymers do not have a hydrophilic character and are thus soluble in oils.

When the copolymer is not sufficiently soluble in the oily phase so as to attain the desired concentration, in the range indicated above, it is possible to improve the solubilization of the copolymer by using an organic co-solvent which is compatible with cosmetologic use. Representative co-solvents include, for example, an alcohol such as ethanol, propanol, isopropanol, glycerol, propylene glycol, and the like. The co-solvent is added to the oily phase before mixing with the aqueous phase of the emulsion.

Generally, the amount of co-solvent, when it is present, is not greater than 30 volume percent relative to the volume of the oily phase.

The oily phase is constituted by oils or mixtures of oils conventionally employed in cosmetic formulations. These oils and their properties are described in specialized literature. They are principally the triglycerides, silicones, hydrocarbons and the like.

Representative oils include, for example, those which are mentioned in the following experimental portion of this specification.

The copolymers employed as thickening agents, in accordance with the invention, exhibit properties of surfactants. When the surfactant properties are insufficient to permit the attainment of a stable emulsion, it is necessary to envisage, in the cosmetic composition or cosmetic composition support, the presence of a conventional emulsifying agent, in an amount sufficient to provide a stable emulsion.

The emulsifying agents compatible with cosmetologic usage are known and described in specialized literature.

Representative useful emulsifying agents include, as non-limiting examples, glycerol isostearate sold by Dynamit Nobel under the trade name "IMITOR 780K" and polyglycerol ethers having the following formula:

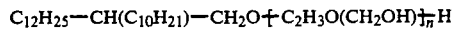
$C_{12}H_{25}-CH(C_{10}H_{21})-CH_2O+C_2H_3O(CH_2OH)\frac{1}{n}H$ wherein n=2 to 15 (statistical value), which are described in French patent application 87.00 878 (2.593.509).

Generally, the amount of the emulsifying agent, when it is present, ranges up to 15 weight percent relative to the total weight of the cosmetic composition or cosmetic composition support.

The cosmetic compositions in accordance with the present invention can contain conventional ingredients (active ingredients, perfumes, preservatives, sunscreen agents and the like).

These ingredients can be added, in accordance with known techniques, either before, during or after the production of the emulsion.

The cosmetic compositions containing the thickened emulsions of the water-in-oil type, produced in accordance with the present invention, have an agreeable appearance. Their texture is light and, contrary to known emulsions of this type, they are not too oily, principally to the touch. Moreover, they penetrate the skin well and they leave, on application to the skin, a freshness sensation.

They can be use for the care and hydration of the face and body and also as a care product for the hands.

The cosmetic composition supports in accordance with the present invention, can also serve as a base, for example, for the production of compositions for protection against solar rays.

The present invention also relates to the use, as a thickening agent, in the preparation of cosmetic compositions or cosmetic composition supports, in the form of water-in-oil type emulsions, at least one copolymer such as defined above.

The present invention also relates to a process for preparing a cosmetic composition or a cosmetic composition support, in the form of a thickened emulsion of the water-in-oil type, this process being characterized by the fact that there is incorporated in the cosmetic composition or cosmetic composition support, as a thickening agent, at least one copolymer such as defined above. Preferably, the thickening agent is incorporated in the oily phase, optionally with a co-solvent as indicated previously, before the production of the emulsion. If desired, a conventional emulsifying agent can be added to improve the stability of the emulsion, as indicated above.

The following non-limiting examples illustrate the present invention:

EXAMPLES OF PREPARATION

Example 1

Copolymer of N-dodecylacrylamide (96.5 weight percent/2-acrylamido-2-methyl-2-propane sulfonic acid (AMPS) (3.5 weight percent); sodium salt In a reactor provided with a mechanical stirrer and a nitrogen bubbler, 96.5 g of N-dodecylacrylamide and 240 g of toluene are introduced and dissolved with stirring at 35° C.

In a parallel manner, a solution of 3.5 g of AMPS in 60 g of methanol, is produced by dissolving, with stirring, at 30° C.

The methanolic solution, maintained at 30° C., is introduced into the reactor maintained with stirring at 35° C. The two solutions mix immediately and produce a clear medium.

1 g of azobisisobutyronitrile initiator is added and the reaction medium is heated, with stirring, up to reflux (66° C.).

These conditions are maintained for 8 hours, after which the reaction medium is permitted to cool to ambient temperature.

The polymerization solution is concentrated using a rotary evaporator initially under a pressure in the order of 20 mm Hg (1 mm Hg corresponds to a pressure of about 130 Pa) and at 35° C. until the appearance of a gel (distillation of 70 g of solvent).

The evaporation is continued under a pressure of about 5 mm Hg at 35° C. until the production of a residue of 160 g which corresponds to a polymer-solvent mixture having a solid appearance.

640 g of tetrahydrofuran are then added and the mixture is stirred until dissolution at ambient temperature.

Once the solution is obtained a portion thereof is retained for analysis. The portion retained is precipitated in water and then dried under a vacuum at ambient temperature.

A volumetric dosage of the acid units is made in a toluene/methanol mixture (95:5 by volume) by using soda (0.1N methanolic solution) and an alizarin/thymol phthalein mixture as a colored indicator. The acid index found is 15 meq. of acid/100 g of polymer.

Neutralization by soda

The polymer solution in tetrahydrofuran is neutralized with stirring at ambient temperature using a stoichiometric amount of sodium hydroxide (in 1N methanolic solution) which amount corresponds to a total neutralization of the sulfonic acid units.

The neutralized solution is concentrated with a rotary evaporator at 35° C. under a pressure of 20 mm Hg until a weight of 300 g is achieved.

The concentrated solution is precipitated in 4 liters of permutted water, cooled at 10° C.

The resulting precipitate is dried under a vacuum at 50° C. until a constant weight is achieved.

Weight obtained: 84 g

Elemental analysis of the neutralized polymer:

| Element | C % | H % | N % | O % | S % | Na % |
|---|---|---|---|---|---|---|
| Theoretical | 73.82 | 11.86 | 5.86 | 7.51 | 0.54 | 0.39 |
| Found | 72.36 | 11.85 | 5.69 | 8.94 | 0.50 | 0.48 |

EXAMPLE 2

Copolymer of N-tert.butylacrylamide (97.9 weight percent)/2-acrylamido-2-methyl propane sulfonic acid (2.1 weight percent); sodium salt.

Into a reactor provided with a mechanical stirrer and a nitrogen bubbler 97.9 g of N-tert.butylacrylamide and 210 g of absolute ethanol are introduced. The mixture is stirred at ambient temperature until dissolution.

In a parallel manner a solution of 2.1 g of 2-acrylamido-2-methyl propane sulfonic acid (AMPS) in 90 g of permutted water is prepared.

The aqueous solution is introduced into the reactor with stirring and 1 g of azobisisobutyronitrile initiator is added.

The reaction mixture is heated to a temperature lower than 70° C. and stirring is maintained at 70° C. for 8 hours.

The reaction medium is cooled and 70 g of absolute ethanol are added when the temperature drops to 55° C., thereby avoiding precipitation of the polymer.

The solution then remains clear up to ambient temperature.

Before neutralization a portion of the solution is retained and is precipitated in cold water. The precipitate is dried under a vacuum at ambient temperature. The acid index, using the method described in Example 1, is 5 meq/100 g of polymer.

The polymer solution is neutralized, with stirring at ambient temperature, by adding a stoichiometric quantity of 1N aqueous soda which quantity corresponds to a total neutralization. This neutralization reaction lasts for one hour.

The neutralized solution is then precipitated in 5 liters of permutted water to which ice has been added. The precipitate is oven dried at 50° C. under a vacuum.

Weight obtained: 90 g

Elemental analysis of the acid polymer (before neutralization).

| Element | C % | H % | N % | O % | S % |
|---|---|---|---|---|---|
| Theoretical | 65.60 | 10.15 | 10.93 | 12.99 | 0.33 |
| Found | 62.62 | 10.17 | 10.63 | 15.28 | 0.33 |

Example 3

Copolymer of N-tert. butylacrylamide (98 weight percent)/3-acrylamido-3-methyl butanoic acid (2 weight percent); sodium salt and triethanolamine salt Into a reactor provided with a mechanical stirrer and a nitrogen bubbler 2 g of 3-acrylamido-3-methyl butanoic acid, 98 g of N-tert.butylacrylamide, 90 g of absolute ethanol, 10 g of permutted water and 0.25 g of azobisisobutyronitrile initiator are introduced. The reaction proceeds with stirring and nitrogen bubbling at 55° C. for 19 hours. When the reaction medium returns to ambient temperature, it is diluted with a mixture constituted of 180 g of ethanol and 80 g of water. 4 liters of ice water are then added.

The resulting precipitate is dried under a vacuum at 50° C.

Weight obtained: 97g — Yield: 99.7%

Acid index by potentiometry: 14.7 meq/100 g or polymer.

The final neutralization is made in situ in the mixture of oil that is to be emulsified, by introducing either the stoichiometric amount of soda (methanolic solution) or the stoichiometric amount of triethanolamine.

EXAMPLE 4

Copolymer of stearyl methacrylate (92.2 weight percent)/2-sulfoethyl methacrylate (7.8 weight percent); sodium salt Into a reactor provided with a mechanical stirrer and a nitrogen bubbler 46.1 g of stearyl methacrylate and 70 g of toluene are introduced.

A clear solution is obtained by stirring at ambient temperature.

In a parallel manner there are dissolved, with stirring at ambient temperature, 3.9 g of 2-sulfoethyl methacrylate in 40 g of ethanol.

The ethanolic solution is introduced into the reactor and is mixed, with stirring, to obtain a homogeneous medium. 0.75 g of azobisisobutyronitrile initiator is then added.

The reaction mixture is heated to 70° C. with stirring and nitrogen bubbling.

23.5 g of toluene are also added to the reaction medium, by portions, over the first three hours of the reaction, so that the medium remains homogeneous. The reaction proceeds for 12 hours in total at 70° C.

When the reaction medium is cooled to ambient temperature at the end of the reaction toluene must again be added in an amount sufficient to avoid the precipitation of the polymer formed in the reactor.

A retained portion of the polymerization solution is precipitated in methanol for analysis.

The retained portion is dried under a vacuum at ambient temperature. The acid index following the method described in Example 1 is 31.4 meq/100 g of polymer.

Neutralization of the polymerization solution by soda.

There is slowly added, with stirring and at ambient temperature, the stoichiometric amount of soda (1N methanolic solution) which amount corresponds to total neutralization and by diluting the reaction medium, if necessary, with toluene to avoid precipitation of the polymer.

The neutralized polymer is purified by precipitation in 3 liters of methanol cooled to 10° C., and then dried under a vacuum at 50° C.

Weight obtained: 26.7 g.

EXAMPLE 5

Synthesis of a copolymer of N-dodecylacrylamide/styrene zinc sulfonate (1) Copolymerization of dodecylacrylamide/styrene Into a reactor provided with a central stirrer and nitrogen bubbler 293.3 g of dodecylacrylamide, 6.7 g of styrene, 150 g of ethyl acetate and 0.75 g of azobisisobutyronitrile initiator are introduced. The mixture is dissolved with stirring and nitrogen bubbling, and it is then heated to 77° C. The polymerization is carried out at this temperature, with stirring and nitrogen bubbling, for 20 hours.

After cooling to ambient temperature, the resulting polymer is purified by precipitation in 5 liters of methanol. The resulting precipitate is dried under a vacuum at 50.C.

Weight obtained: 292.5 g (yield: 97.5%)

(2) Sulfonation of styrene units 100 g of the preceding polymer are dissolved in 600 g of 1,2-dichloroethane with stirring. The total dissolution requires several hours.

The resulting solution is heated to 53° C. with nitrogen bubbling and there are successively introduced 2730 microliters of acetic anhydride and then 1000 microliters of 95% sulfuric acid.

The reaction proceeds, with stirring at 50° C. and under nitrogen bubbling. 50 g of absolute ethanol are added to the reaction medium at 50° C. to stop the reaction. The reaction medium is then cooled to ambient temperature.

This sulfonation solution is slowly poured into 4 liters of boiling water (flash distillation). The white precipitate is recovered in the form of a compact mass, which is submitted to grinding in the presence of 1 liter of permutted water. The polymer is thus provided in the form of compact grains which are dried by lyophilization.

Weight obtained: 97 g.

The acid index following the method described in Example 1 is 9 meq/100 g of polymer.

(3) Total neutralization of sulfonic acid units by zinc acetate 40 g of the acid polymer from the preceding stage are dissolved in 360 ml of toluene and 40 ml of n-propanol are added.

The resulting solution is heated to 90.C under nitrogen bubbling. 1.37 g of zinc acetate (dihydrate) are added and the reaction proceeds, with stirring, at 90° C. for 3 hours.

The final solution is cooled and precipitated in 5 liters of methanol. The precipitate is dried at 50° C. under a vacuum.

Weight obtained: 35.7 g

Example 6

Synthesis of a copolymer of N-octadecylacrylamide (96.5 weight percent)/2 -acrylamido-2-methyl propane sulfonic acid (AMPS) (3.5 weight percent); sodium salt Into a reactor provided with a mechanical stirrer and a nitrogen bubbler 44.2 g of N-octadecyl acrylamide and 110 g of toluene are introduced and are dissolved with stirring at ambient temperature.

In a parallel manner, and at ambient temperature, a solution of 1.6 g of 2-acrylamido-2-methyl propane sulfonic acid (AMPS) in 27.5 g of methanol is produced.

The methanolic solution is introduced into the reactor and is mixed with the contents thereof, with stirring and nitrogen bubbling.

0.458 g of azobisisobutyronitrile initiator is added and the reaction medium is heated at 60.C with stirring and nitrogen bubbling. The polymerization reaction proceeds under these conditions for 12 hours.

The polymer solution is concentrated to the maximum by evaporation under a vacuum following the procedures of Example 1.

The residue is dissolved in 105 g of tetrahydrofuran at ambient temperature.

A retained portion is precipitated in methanol for analysis and dried under a vacuum at ambient temperature.

The acid index of the retained portion, following the dosage employed in Example 1, is 14.5 meq/100 g of polymer.

Elemental analysis of the retained portion:

| Element | C % | H % | N % | O % | S % |
| --- | --- | --- | --- | --- | --- |
| Theoretical | 76.71 | 12.47 | 4.42 | 5.86 | 0.54 |
| Found | 74.95 | 12.79 | 4.35 | 7.40 | 0.49 |

Total neutralization by soda: 150 g of the solution in tetrahydrofuran are neutralized with stirring at ambient temperature by the amount of soda (1N methanolic solution) which corresponds to total neutralization. This neutralization reaction proceeds with stirring for 1 hour.

The sodium salt is purified by precipitation in 2 liters of methanol and then dried under a vacuum at 50° C. until constant weight is achieved.

Weight obtained: 32.5 g

EXAMPLES OF USE

Production and study of water-in-oil emulsions thickened with the polymers in accordance with the present invention The emulsions are all prepared under the same conditions.

The polymer which produces the thickening of the emulsion is dissolved in the selected oil or mixture of oils in the presence of an emulsifier and the amount of alcohol required for solubilization (ethanol, isopropanol, propylene glycol and the like).

The dissolution is carried out at ambient temperature with stirring or more easily by heating with stirring without evaporation of the alcohol.

The aqueous phase preferably contains magnesium sulfate, $MgSO_4 \cdot 7H_2O$ to obtain better stability.

The emulsion is produced at ambient temperature by using a Moritz disperser (commercial name) operated at 3,000 rpm with progressive introduction of the aqueous phase in the organic phase. The emulsion can also be produced at a more elevated temperature (lower than 100° C.) with preheating of the two phases. In this situation propylene glycol is preferably employed to dissolve the polymer in the organic phase.

The viscosity of the emulsion is measured with a Contraves viscometer (commercial name) at 25° C.

The data on the constituents of the emulsions and on the resulting viscosities are set forth in Table 1 below.

Abbreviated notations:

ET: ethanol; IP: isopropanol; PG: propylene glycol; PIB: hydrogenated polyisobutylene sold by Nichiya under the mark "PARLEAM"; HP: paraffin oil; HT: turnsole oil; HK: Kerite oil; MIP: isopropyl myristate; FNS: $C_{12}$-$C_{15}$ alkyl benzoate sold by Witco under the mark "FINSOLV TN"; CPDS: cyclopentadimethyl siloxane, silicone oil sold by Union Carbide; IMW: glyceride partially modified by isostearic acid, sold by Dynamit Nobel under the mark "IMWITOR-780k'"; EPG: polyglycerolether having the formula:

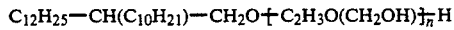

wherein n=3 (statistical value).

All the emulsions have been prepared at ambient temperature, except in the case of Example C (80° C.).

The polymer employed in Example K is that of Example 3 (1 g) neutralized in situ with triethanolamine (TEA: 22 mg).

What is claimed is:

1. A cosmetic composition comprising a water-in-oil emulsion in the form of a thick cream, said composition containing a thickening agent in an amount such that the viscosity of said cream is greater than 1.5 Pa.s., said thickening agent comprising a copolymer having (a) units of the formula

wherein

M is an atom of oxygen or a —$N(R_3)$— group,
$R_1$ represents hydrogen or —$CH_3$,
$R_2$ represents a saturated, linear or branched hydrocarbon chain having 4–22 carbon atoms,
$R_3$ represents hydrogen or a saturated, linear or branched hydrocarbon chain having 1–22 carbon atoms, and (b) units of the formula,

wherein (i) $R_4$ represents hydrogen or —$CH_3$ and $R_5$ represents —CO—X—Z—Y, wherein X represents an atom of oxygen or —$N(R_6)$—, $R_6$ represents hydrogen or a saturated hydrocarbon chain having 1–22 carbon atoms, Z represents a saturated, linear or branched hydrocarbon chain having 2–22 carbon atoms or a saturated, linear or branched hydrocarbon chain having 2–22 carbon atoms and interrupted by a —NH-group or an —O-heteroatom, and Y represents —COOH or —$SO_3H$, or (ii) $R_4$ represents hydrogen and $R_5$ represents —$SO_3H$, —$CH_2SO_3H$ or —$C_6H_4$—$SIO_3H$, the said copolymer containing, in units, from 90 to 99 percent of units of formula I, the remaining units being units of formula II, and the said —COOH, —$SO_3H$, —$CH_2SO_3H$ and —$C_6H_4SO_3H$ groups are in partially or completely salified form, and when $R_5$ represents —$C_6H_4SO_3H$, M represents —$N(R_3)$ wherein $R_3$ has the meaning given above.

2. The composition claim 1 wherein said copolymer is present in an amount ranging from 0.05 to 5 weight percent based on the total weight of said composition.

| Example | Polymer of Example No. | Co-Solvent | Oily Phase | Emulsifier | Water | Magnesium Sulfate | Viscosity Pa.s |
|---|---|---|---|---|---|---|---|
| A | Ex. 1: 1 g | IP: 1 ml | PIB: 28 g |  | 70 g |  | 4.0 |
| B | Ex. 1: 1 g | ET: 1 ml | PIB: 16 g | IMW: 5 g | 76.5 g | 0.5 g | 10 |
| C | Ex. 1: 0.5 g | PG: 0.1 ml | PIB: 16 g | IMW: 5 g | 76.5 g | 2 g | 7 |
| D | Ex. 1: 1 g | ET: 1 ml | PIB: 20 g CPDS: 5 g | IMW: 5 g | 71 g | 2 g | 4.8 |
| E | Ex. 1: 0.5 g | ET: 0.5 ml | HP: 12 g | IMW: 5 g | 75 g | 2 g | 6.5 |
| F | Ex. 1: 0.2 g | ET: 0.2 ml | FNS: 25 g | IMW: 5 g | 67.6 g | 2 g | 6.5 |
| G | Ex. 1: 1 g | ET: 1 ml | HP: 40 g | IMW: 5 g | 51 g | 2 g | 6 |
| H | Ex. 1: 0.2 g | ET: 0.2 ml | HK: 45 g | IMW: 5 g | 47.6 g | 2 g | 7.3 |
| I | Ex. 1: 2 g | ET: 2 ml | PIB: 18 g | EPG: 3 g | 74 g | 1 g | 7.3 |
| J | Ex. 2: 1 g | ET: 1 ml | HP: 18 g | IMW: 5 g | 73 g | 2 g | 7 |
| K | Ex. 3: 1.022 g | ET: 1 ml | MIP: 20 g | IMW: 5 g | 71 g | 2 g | 3.1 |
| L | Ex. 4: 2 g | ET: 0.2 ml | PIB: 48 g |  | 50 g |  | 2 |
| M | Ex. 5: 1 g | IP: 3 ml | HP: 25 g |  | 68.6 g |  | 2.8 |
| N | Ex. 6: 1 g |  | PIB: 20 g | IMW: 5 g | 72 g | 2 g | 7.5 |

3. A cosmetic composition comprising a water-in-oil emulsion in the form of a thick cream, said composition containing a thickening agent comprising a copolymer having (a) units of the formula

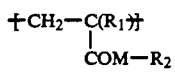

wherein

M is an atom of oxygen or a —N(R$_3$)—group,

R$_1$ represents hydrogen or —CH$_3$,

R$_2$ represents a saturated, linear or branched hydrocarbon chain having 4–22 carbon atoms, R$_3$ represents hydrogen or a saturated, linear or branched hydrocarbon chain having 1–22 carbon atoms, and (b) units of the formula

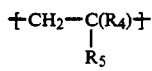

wherein (i) R$_4$ represents hydrogen or —CH$_3$ and R$_5$ represents —CO—X—Z—Y, wherein X represents an atom of oxygen or —N(R$_6$)—, R$_6$ represents hydrogen or a saturated hydrocarbon chain having 1–22 carbon atoms, Z represents a saturated, linear or branched hydrocarbon chain having 2–22 carbon atoms or a saturated, linear or branched hydrocarbon chain having 2–22 carbon atoms and interrupted by a —NH-group or an —O-heteroatom, and Y represents —COOH or —SO$_3$H, or (ii) R$_4$ represents hydrogen and R$_5$ represents —SO$_3$H, —CH$_2$SO$_3$H or —C$_6$H$_4$—SO$_3$H, the said copolymer containing, in units, from 90 to 99 percent of units of formula I, the remaining units being units of formula II, and the said —COOH, —SO$_3$H, —CH$_2$SO$_3$H and —C$_6$H$_4$SO$_3$H groups are in partially or completely salified form, and when R$_5$ represents —C$_6$H$_4$SO$_3$H, M represents —N(R$_3$) wherein R$_3$ has the meaning given above, and the said copolymer being present in an amount ranging from 0.05 to 5 weight percent based on the total weight of said composition.

4. The composition claim 3 wherein said copolymer does not contain any —SO$_3$H groups, free or salified.

5. The composition claim 3 wherein said copolymer does not contain any —COOH groups, free or salified.

6. The composition claim 3 wherein the units of formula I are derived from at least one monomer selected from the group consisting of hexyl acrylate, 2-ethyl hexyl acrylate, dodecyl acrylate, octadecyl acrylate, hexyl methacrylate, 2-ethyl hexyl methacrylate, dodecyl methacrylate, octadecyl methacrylate, hexyl acrylamide, 2-ethylhexyl acrylamide, dodecyl acrylamide, octadecyl acrylamide, hexyl methacrylamide, 2-ethyl-hexyl methacrylamide, dodecyl methacrylamide, octadecyl methacrylamide, N-ethyl-N-dodecyl acrylamide, N-ethyl-N-dodecyl methacrylamide, N-butyl-N-dodecyl acrylamide and N-butyl-N-dodecyl methacrylamide.

7. The composition claim 3 wherein the units of formula II are derived from at least selected from the group consisting of 2-acrylamido-2-methyl propane sulfonic acid, (10-acrylamido-10-methyl) decanoate of 2-sulfoethyl, 2-sulfoethyl methacrylate, vinyl sulfonic acid and allyl sulfonic acid.

8. The composition claim 3 wherein said copolymer has a molecular mass between 5,000 and 500,000.

9. The composition claim 3 wherein said —COOH or —SO$_3$H groups or both are salified in the form of a metallic salt or an amine salt.

10. The composition of claim 9 wherein said metallic salt is an alkali metal salt, an alkaline earth metal salt or a zinc salt.

11. The composition of claim 10 wherein said metallic salt is a lithium, potassium, sodium, zinc, calcium or magnesium salt.

12. The composition of claim 9 wherein said amine salt is a salt of triethanolamine, 2-amino-2-methyl-1-propanol or 2-amino-2-methyl-1,3-propanediol.

13. The composition claim 3 wherein said copolymer is present in an amount ranging from 0.1 to 2 weight percent based on the total weight of said composition.

14. The composition claim 3 wherein the oil phase of said emulsion contains a co-solvent to improve the solubility of said copolymer.

15. The composition of claim 14 wherein said co-solvent is an alcohol selected from the group consisting of ethanol, propanol, isopropanol, glycerol and propylene glycol.

16. The composition of claim 14 wherein said co-solvent is present in an amount not exceeding 30 volume percent relative to the volume of said oil phase.

17. A process for preparing a cosmetic composition comprising a water-in-oil emulsion in the form of a thick cream, said process comprising incorporating into the oil phase of said water-in-oil emulsion 0.05 to 5 weight percent based on the total weight of said composition a thickening agent comprising a copolymer having (a) units of the formula

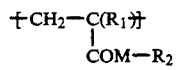

wherein

M is an atom of oxygen or a —N(R$_3$)-group,

R$_1$ represents hydrogen or —CH$_3$,

R$_2$ represents a saturated, linear or branched hydrocarbon chain having 4–22 carbon atoms, R$_3$ represents hydrogen or a saturated, linear or branched hydrocarbon chain having 1–22 carbon atoms, and (b) units of the formula

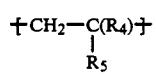

wherein (i) R$_4$ represents hydrogen or —CH$_3$ and R$_5$ represents —CO—X—Z—Y, wherein X represents an atom of oxygen or —N(R$_6$)—, R$_6$ represents hydrogen or a saturated hydrocarbon chain having 1–22 carbon atoms, Z represents a saturated, linear or branched hydrocarbon chain having 2–22 carbon atoms or a saturated, linear or branched hydrocarbon chain having 2–22 carbon atoms and interrupted by a —NH-group or an —O-heteroatom, and Y represents —COOH or —SO$_3$H, or
(ii) R$_4$ represents hydrogen and R$_5$ represents —SO$_3$H, —CH$_2$SO$_3$H or —C$_6$H$_4$—SO$_3$H,
the said copolymer containing, in units, from 90 to 99 percent of units of formula I, the remaining units being units of formula II, and the said —COOH, —SO$_3$H, —CH$_2$SO$_3$H and —C$_6$H$_4$SO$_3$H groups are in partially or completely salified form, and when R$_5$ represents —C$_6$H$_4$SO$_3$H, M represents —N(R$_3$) wherein R$_3$ has the meaning given above.

* * * * *